United States Patent [19]

Tausch et al.

[11] 4,240,752

[45] Dec. 23, 1980

[54] PROCESS AND APPARATUS FOR RECOGNIZING CLOUD DISTURBANCES IN A SAMPLE SOLUTION WHICH IS BEING SUBJECTED TO ABSORPTION PHOTOMETRY

[75] Inventors: Walter Tausch; Hans Gausmann, both of Aalen, Fed. Rep. of Germany

[73] Assignee: Carl Zeiss-Stiftung, Oberkochen, Fed. Rep. of Germany

[21] Appl. No.: 957,150

[22] Filed: Nov. 3, 1978

[30] Foreign Application Priority Data

Dec. 22, 1977 [DE] Fed. Rep. of Germany ....... 2757197

[51] Int. Cl.³ ............................................ G01N 21/00
[52] U.S. Cl. ..................................... 356/436; 250/574
[58] Field of Search ............................... 356/432–442; 250/574

[56] References Cited

U.S. PATENT DOCUMENTS

| | | | |
|---|---|---|---|
| 2,572,008 | 6/1946 | Cahusac | 340/630 X |
| 3,358,148 | 12/1967 | Conklin et al. | 356/436 X |

Primary Examiner—John K. Corbin
Assistant Examiner—Bruce Y. Arnold
Attorney, Agent, or Firm—Hopgood, Calimafde, Kalil, Blaustein & Lieberman

[57] ABSTRACT

The invention contemplates continuous monitoring of a sample solution for cloud disturbances while conducting absorption-photometry measurements on the solution. The absorption-photometry measurements are a function of light directly transmitted through the sample solution, and the cloud disturbances are observed to the extent that the same light is or may be dispersed by cloud particles, in one lateral direction from the direct-transmission axis.

4 Claims, 1 Drawing Figure

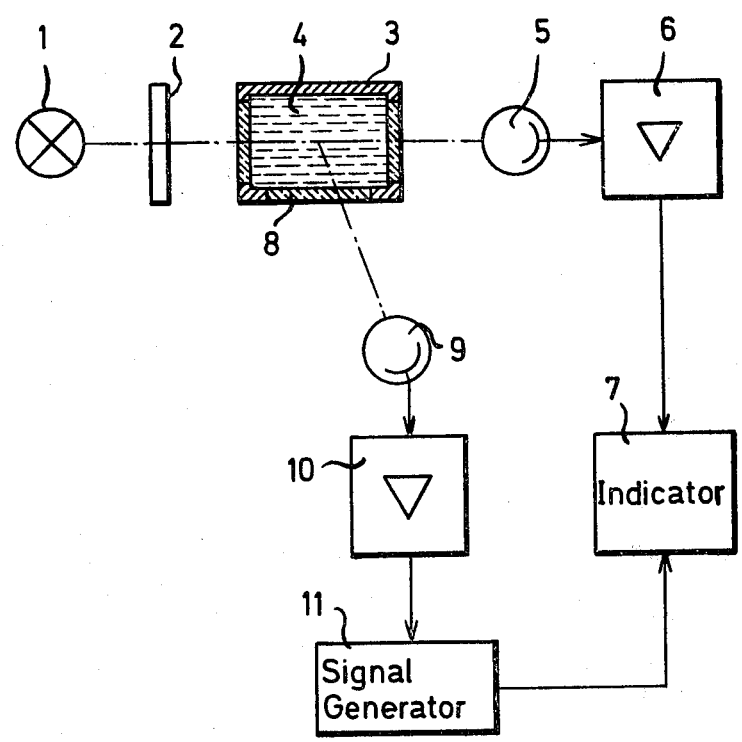

PROCESS AND APPARATUS FOR RECOGNIZING CLOUD DISTURBANCES IN A SAMPLE SOLUTION WHICH IS BEING SUBJECTED TO ABSORPTION PHOTOMETRY

The present invention concerns a process for recognizing such cloud disturbances as may occur in an absorption-photometry sample solution, and to apparatus for carrying out the process.

In absorption photometry, radiation, preferably light, is passed through a cell containing a sample solution, and the absorption of this radiation is measured. From the measured absorption, the concentration of the sample solution is calculated by the Lambert-Beer law. In order to be able to apply this law, it is necessary, on the one hand, that the sample solution be present in the form of a dilute solution and that the radiation passing through this solution does not experience any dispersion losses. Such dispersion losses occur when the sample solution contains a cloud disturbance.

In so-called automatic analyzers, the specimen to be analyzed is automatically prepared for the measurement and is brought into the measurement-ray path. The subsequent measurement also takes place automatically. It is clear that an evaluation based on absorption measurement leads to erroneous results if a cloud disturbance is present in the sample solution being measured. Such clouds cannot be recognized in the case of automatic analyzers due to the automatic nature of preparing and measuring the sample, so that unrecognized erroneous results can occur.

The object of the present invention is to provide a method and apparatus for achieving automatic recognition of such cloud disturbances as may occur in a sample solution which is being subjected to absorption-photometry measurement.

This purpose is achieved, in accordance with the invention, by measuring and indicating the presence of such radiation as may be scattered laterally at a predetermined angle to the path of the light ray which is being concurrently used for making the absorption measurement.

If a sample solution contains a disturbing cloud, the measurement radiation is scattered by the particles which cause the cloud, i.e., a certain stray-radiation proportion occurs laterally to the measurement radiation which passes through the sample. This stray radiation need not necessarily be measured in the new method; it may be merely noted and used to produce an indication or to give off a warning signal.

The new method can be used to particular advantage for the automatic measurement of a series of samples. In this case, it may happen that, at times, an unforeseeable cloud is present in a series of samples, which cloud would falsify the measurement result.

The apparatus for carrying out the new process is characterized by the fact that the cell which serves to receive the sample to be measured has a side window, and that a radiation receiver connected with an indicating element is arranged on that side of the cell. By suitable spatial arrangement of the lateral window and of the corresponding receiver, the angle between the transmitted-light direction and the direction of stray radiation can be determined and measured.

The invention will be described in further detail in connection with the accompanying drawing, which schematically shows an illustrative embodiment of an absorption-photometer apparatus in accordance with the invention, it being understood that, for simplicity, all optical components have been omitted.

In the drawing, light from a source 1 passes through a filter or monochromator 2 and then goes through a cell 3 which contains the sample solution 4 to be measured. Light which passes through the sample solution 4 impinges upon a radiation receiver 5. The signal output of said receiver is amplified and processed in an amplifier 6 and is indicated for measurement purposes at an indicating device 7. The electronic components 6 and 7 are so devised that the indication preferably directly indicates the concentration in the sample solution 4 of the element sought therein.

One side wall of the cell 3 includes a window 8 through which no light passes if the sample solution 4 is clear. However, if the sample solution 4 contains cloud particles, then light dispersed by said particles emerges through the window 8 and strikes a photoelectric receiver 9. The signal output of receiver 9 is amplified and processed in an amplifier 10 and is then fed to a signal generator 11. The latter is preferably so developed that upon the occurrence of a signal output from the receiver 9, the signal generator produces an optical or acoustic warning signal. However, it is also possible to connect the signal generator 11 directly to the indicating unit 7 (as shown) so that, together with the absorption-photometry indication at 7, an indication is given as to the presence of a cloud disturbance.

As noted above, optical elements have been omitted from the drawing, but the dash-dot line between cell window 8 and receiver 9 will be understood to suggest optical means which focuses light emerging through window 8 onto the photocathode of the receiver 9.

What is claimed is:

1. In apparatus for making absorption-photometric measurements upon a series of liquid samples wherein light from a source is transmitted on a first and direct path alignment through the same, there being concentration-measurement means including a photoelectric receiver positioned for response to light passing through the sample on said alignment, and means directly connected to the output of said photoelectric receiver for providing a direct indication of the concentration of a sought element in each of a succession of the samples, the improvement wherein a further photoelectric receiver and associated optical-focusing means are positioned laterally of said path alignment and are optically aligned to intersect said direct path alignment within the sample, and means independent of said concentration-measurement means and responsive to a signal output of said further photoelectric receiver for indicating for the case of each absorption measurement whether a cloud disturbance is present in the sample.

2. The improvement of claim 1, in which a single indicator means has separate inputs connected to the respective outputs of said photoelectric receivers for concurrent indication of both the concentration measurement and whether a cloud disturbance is present at the time of making the concentration measurement.

3. In a process for automatically measuring a series of sample solutions by absorption photometry along a measuring lightbeam alignment, the improvement wherein the sample solutions are continuously monitored for cloud disturbances by independently measuring and indicating the radiation dispersed laterally of the measuring light beam at a predetermined angle to said alignment.

4. The improvement of claim 3, characterized by the fact that a warning signal is given off upon the detection of laterally dispersed radiation.

* * * * *